(12) United States Patent
Schreiber

(10) Patent No.: US 6,844,333 B1
(45) Date of Patent: Jan. 18, 2005

(54) METHOD OF TREATING ATHEROSCLEROSIS

(75) Inventor: Alan D. Schreiber, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 09/535,951

(22) Filed: Mar. 27, 2000

Related U.S. Application Data
(60) Provisional application No. 60/126,407, filed on Mar. 26, 1999.

(51) Int. Cl.[7] .............................................. A61K 31/56
(52) U.S. Cl. ..................................................... 514/178
(58) Field of Search ............................... 514/178, 177, 514/171, 327

(56) References Cited

U.S. PATENT DOCUMENTS

| | | | |
|---|---|---|---|
| 4,444,778 A | * 4/1984 | Coughlin | |
| 4,902,681 A | 2/1990 | Schreiber | |
| 4,908,358 A | 3/1990 | Schreiber | |
| 5,075,321 A | 12/1991 | Schreiber | |
| 5,679,666 A | * 10/1997 | Clark | 514/179 |
| 5,716,981 A | * 2/1998 | Hunter et al. | 514/449 |

FOREIGN PATENT DOCUMENTS

WO     WO96/09826    * 4/1996

OTHER PUBLICATIONS

Kuzuya et al., J Cell Physiol, 1995; 164(3):658–667.*
de Gruijter et al., Abstract of Metabolism, 1991; 40(11):119–1121.*
Blei et al., Journal of Cellular Physiology, 1993; 155:568–578.*
de Gruijter et al., Metabolism, 1991; 40(11):1119–1121.*
Pels et al., Jpn. Circ. J., 1997;61:893–904.*
O'Brien et al., American Journal of pathology, 1994;145(4):883–894.*
Physician's Desk Reference, pp. 2506–2507 (1999).
Physician's Desk Reference, pp. 867–868 (1999).
Michael and Zumpe, "Medroxyprogesterone Acetate Decreases the Sexual Activity of Male Cynomolgus Monkeys (*Macaca fascicularis*): An Action on the Brain?", Physiology & Behavior 53:783–788 (1993).
Wright et al., "Medroxyprogesterone Acetate and Reproductive Processes in Male Dogs", Australian Veterinary Journal 55:437–438 (1979).
Zumpe et al, "Medroxyprogesterone Acetate, Aggression, and Sexual Behavior in Male Cynomolgus Monkeys (*Macaca fascicularis*)", Hormones and Behavior 25:394–409 (1991).
Meter et al, "Physical, metabolic, and hormonal effects on men of long–term therapy with medroxprogesterone acetate", Fertility and Sterility 43(1):102–109 (1985).
Linn and Steklis, "The Effects of Depo–Medroxyprogesterone Acetate (DMPA) on Copulation–Related and Agonistic Behaviors in an Island Colony of Stumptail Macaques (*Macaca arctoides*)", Physioloty & Behavior 47:403–408 (1990).
Spagnoli et al, "High–dose synthetic progestogens inhibit foam and smooth muscle cell proliferation and atherosclerotic plaque formation in aortas of rabbits fed a hypercholesterolemic diet", Tuberculosis 82:27–36 (1990).

(List continued on next page.)

Primary Examiner—San-ming Hui
(74) Attorney, Agent, or Firm—Nixon & Vanderhye P.C.

(57) ABSTRACT

The present invention relates to a method of treating atherosclerosis, and to compounds and compositions suitable for use in such a method.

2 Claims, 1 Drawing Sheet

OTHER PUBLICATIONS

Croxatto et al, "Effect of a Sequential Regimen of Mifepristone–Medroxyprogesterone Acetate on Ovarian Function, Endometrial Development and Hormonal Parameters", Contraception 54(2):79–86 (1996).
Terenius, "Affinities of Progestogen and Estrogen Receptors in Rabbit Uterus for Synthetic Progestogens", Steroids 23(6):909–919 (1974).
Whitehead et al, "The Role and Use of Progestogens", Obstetrics and Gynecology 75(4 (Suppl):59S–76S (1990).
Houser et al, "Serum Lipids and Arterial Plaque Load are Altered Independently By Exogenous Estrogen and Progesterone in Hypercholesterolemic Male Rabbits", Annual Meeting Abstracts 37A—Abstract No. 198.
Arar et al, Galectin–3 gene (LGALS3) expression in experimental atherosclerosis and cultured smooth muscle cells, FEBS Letters 430:307–311 (1998).
Bickell and Freeman, "Rabbit Aortic Smooth Muscle Cells Express Inducible Macrophage Scavenger Receptor Messenger RNA That Is Absent from Endothelial Cells", J. Clin. Invest. 90:1450–1457 (1992).
Saku et al, "Lack of effect of chlorpromazine and haloperidol on serum lipid levels and on atherogenesis in cholesterol fed rabbits", Artery 16(3):151–158 (1989)—Abstract.
Vaisanen et a, "Haloperidol, thioridazine and placebo in mentally subnormal patients–serum levels and clinical effects", Acta Psychiatr. Scand. 63(3):262–271 (1981)—Abstract.
Inano et al, "Estradiol–17 beta as an initiation modifier for radiation–induced mammary tumorigenesis of rats ovariectomized before puberty", Carcinogenesis 16(8):1871–1877 (1995)—Abstract.
Palermo–Neto and Dorce, "Influences of estrogen and/or progesterone on some dopamine related behavior in rats", Gen. Pharmacol. 21(1):83–87 (1990)—Abtract.
Carrillo et al, "Dopaminergic stimulation of pituitary but not hypothalamic estrogen receptors in overiectomized rats", Endocrinology 112(5):1839–1846 (1983)—Abstract.
Hwang and How, "Antiestrogen–binding sites in 7,12–dimethylbenz(a)anthracene–induced rat mammary tumors" relation to growth, Oncology 47(6):495–500 (1990)—Abstract.
Bala and Garg, "Effect of prolonged trifluoperazine, imipramine and haloperidol administration on serum cholesterol. An experimental study in rabbits", Phatmacology 14(5):385–389 (1976)—Abstract.
Van Gent et al, "Haloperidol administration to rats during pregnancy induces permanent alterations in serum lipoprotein patters of progeny", J. Clin. Psychopharmacol. 11(2):113–115 (1991)—Abstract.
O'Connor et al, "An in vivo battery for identifying endocrine modulators that are estrogenic or dopamine regulators", Fundam. Appl. Toxicol. 33(2):182–195 (1996)—Abstract.
Aune et al, "Hormone replacement therapy reduces the reactivity of monocytes and platelets in whole blood–a–beneficial effect on atherogenesis and thrombus formation?", Am. J. Obstet Bynecol. 173:1816–1820 (1995)—Abstract.
Fahmy et al, "Effect of depo–medroxyprogesterone acetate on coagulation factors and serum lipds in Egyptian woman", Contraception 44:431–444 (1991)—Abstract.
Barbieri and Ryan, "Direct effects of medroxyprogesterone acetate (MPA) and megestrol acetate (MGA) on rat testicular steroidogenesis", Acta Endocrinol. (Copenh) 94(3):419–425 (1980)—Abstract.

Wright et al, "Medroxyprogesterone acetate and reproductive processes in male dogs", Aust. Vet. J. 55(9):437–438 (1979)—Abstract.
Barwin, "Recent advances in the pharmaceologic regulation of fertility in men", Can. Med. Assoc. J. 119(7):757–759 (1978)—Abstract.
Hunt et al, "Endocrinological and physiological features after steroid treatment of male rats", Arch. Androl. 1(4):311–320 (1976)—Abstract.
Flickinger, "The influence of progestin and androgen on the fine structure of the male reproductive tract of the rat. II. Epididymis and sex accessory glands", Anat. Rec. 187(4):431–462 (1977)—Abstract.
Lumbiganon, "Depot–medroxyprogesterone acetate (DMPA) and cancer of the endometrium and ovary", Contraception 49(3):203–209 (1994)—Abstract.
Riar et al, "Contraceptive efficacy of Depot Provera jet–injected into the cervix", Indian J. Physiol. Pharmacol. 35(1):21–26 (1991)—Abstract.
Bhiwgade et al, "Effect of depot medroxprogesterone acetate on testis of albino rats: ultrastructural and biochemical studies", Indian J. Exp. Biol. 29(4):319–326 (1991)—Abstract.
Bamberg–Thalen and Linde–Forsberg, "The effects of medroxprogesterone acetate and ethinylestradiol on hemogram, prostate, testes, and semem quality in normal dogs", Xentralbl. Veterinarmed. A. 39(4):264–270 (1992)—Abstract.
Paramo et al, "Effects of medroxyprogesterone acetate of gonadotrophin–releasing hormone agonist on suppression of spermatogenesis in the dog (Canis familiaris)", J. Reprod. Fertil. Suppl. 47:387–397 (1993)—Abstract.
Frick et al, "Steroidal compounds (injectable and implants) affecting spermatogenesis in men", J. Reprod. Feril. Suppl. (24 suppl):35–47 (1976)—Abstract.
Ramanathan et al, "Effects of immature recruitable collaterals on myocardial blood flow and infract size after acute coronary occlusion"; J. Lab. Clin.Med 125:66 (1995).
Pijls et al, "Quantification of Recruitable Coronary Collateral Blood Flow in Conscious Humans and Its Potential to Predict Future Ischemic Events"; J. Am. Coll. Cardiology, 25:1522 (1995).
Williams et al, "Functional Significance of Coronary Collateral Vessels in Patients With Acute Myocardial Infraction: Relation to Pump Performance, Cardiogenic Shock and Survival"; Am. J. Cardiology, 37:345 (1976).
Hansen et al, "Coronary collateral circulation: Clinical significance and influence on survival in patients with coronary artery occlusion"; Am. Heart J. 117:290 (1989).
Habib et al, "Influence of Caronary Collateral Vessels on Myocardial Infract Size in Humans", Circulation 83:739 (1991).
Billinger et al, "Physiologically Assessed Coronary Collateral Flow and Adverse Cardiac Ischemic Events: A Follow8Up Study in 403 Patients With Coronary Artery Disease"; J. Am. Coll. Cardiology, 40:1545 (2002).
Gohlke et al, "Prognostic Importance of Collateral Flow Residual Coronary Stenosis of the Myocardial Infract Artery After Anterior Wall Q–Wave Acute Myocardial Infraction"; Am J. Cardiology, 67:1165 (1991).
Williams et al, "Vasa Vasorum in Atherosclerotic Coronary Arteries: Responses to Vasoactive Stimuli and Regression of Atherosclerosis"; Circulation Res. 62:515 (1988).

Barger et al, "Hypothesis: Vasa Vasorum and Neovascularization of Human Coronary Arteries"; New Eng. J. Med., 310:175 (1984).

Boehrer et al, Influence of Collateral Filing of the Occluded Infarct–Related Coronary Artery on Prognosis after Acute Myocardial Infarction, Am. J. Cardiol. 69:110 (1992).

Barbieri and Ryan, "Direct effects of medroxprogesterone acetate (MPA) and megestrol acetate (MGA) on rat testicular steroidogenesis", Acid Endocrinologica 94:419–425 (1980).

Roubinian et al, "Androgenic Hormones Modulate Autoantibody Responses and Improve Survival in Murine Lupus", The Journal of Clinical Investigation 59:1066–1070 (1977).

Lahita, "Sex Steroids and the Rheumatic Diseases", Arthritis and Rheumatism 28(2):121–126 (1985).

Lahita et al, "Increased Oxidation of Testosterone in Systemic Lupus Erythematosus", Arthritis and Rheumatism 26(12):1517–1521 (1983).

Schreiber et al, "Effect of Endogenous and Synthetic Sex Steroids on the Clearance of Antibody–Coated Cells", The Journal of Immunology 141(9):2959–2966 (1988).

Pritchard and MacDonald, "The Placental Hormones and Their Precursors", Williams Obstetrics, Sixteenth Edition, Pub. Appelton–Century–Crofts, New York, Chapter 7, pp. 147–168.

Haynes, Jr. and Larner, "Adrenocorticotropic Hormone; Adrenocortical Steroids and Their Synthetic Analogs; Inhibitors of Adrenocortical Steroid Biosynthesis", The Pharmacological Basis of Therapeutics, Fifth Edition, Goodman and Gilman, eds., Macmillian Publishing Co., Inc., Chapter 70, pp. 1472–1506 (1976).

Siiteri et al, "Sex Steroids and the Immune System—i. Sex Differnece in Autoimmune Disease in NZB/NZW Hybrid Mice", Journal of Steroid Biochemistry 12:425–432 (1980).

Jungers et al, "Hormonal Modulation in Systemic Lupus Erythematosus", Arthritis and Rheumatism 28(11):1243–1250 (1985).

Duncan, M.R. and Duncan, G.R., "An In Vivo Study of the Action of Antiglucocorticoids on Thymus Weight Ratio, Antobody Titre and the Adrenal–Pituitary–Hypothalamus Axis", Journal of Steroidal Biochemistry 10:245–259 (1979).

Siiteri and Stites, "Immunologic and Endocrine Interrelationships in Pregnancy", Biology of Reproduction 26:1–14 (1982).

* cited by examiner

Haloperidol

SCH-23390

Sulpiride

METHOD OF TREATING ATHEROSCLEROSIS

This application claims priority from Prov. App. No. 60/126,407, filed Mar. 26, 1999. The entire contents of the provisional application is incorporated herein by reference.

TECHNICAL FIELD

The present invention relates to a method of treating atherosclerosis, and to compounds and compositions suitable for use in such a method.

BACKGROUND

Delayed development of coronary artery disease in premenopausal women, compared to that of age-matched men, was noted over sixty years ago (Levy et al, J. Am. MedAssoc. 107:97–102 (1936), Master et al, Arch. Int. Med. 64:767–786 (1939)). Despite numerous reports addressing the antiatherogenic effect of estrogen in premenopausal women and in postmenopausal women on estrogen replacement therapy, the mechanism of this protective effect and its relationship to alteration in serum lipids is still unclear.

Even less is known about the effect of progesterone on the development of atherosclerosis, either alone or in combination with estrogen. Conflicting clinical and experimental data suggest that the effect of exogenous progestogens on the development of coronary artery disease ranges from adverse (Hirvonen et al, N. Engl. J. Med. 304:560–563 (1981)) to null (Adams et al, Arteriosclerosis 10:19051 (19090)) to potentially desirable (Haarbo et al, Am. J. Med. 90:584–589 (1991)) to favorable (Alexandersen et al, Arterioscler Thromb. Vasc. Biol. 18:902–907 (1998)) when combined with estriol treatment. A favorable effect of progesterone treatment alone is not believed to have been documented in a clinical study.

Various animal models used to study the effects of sex steroids on the development of atherosclerosis have demonstrated beneficial results associated with exogenous estrogen with or without progesterone in chickens (Pick et al, Circulation 6:276–280 (1952), Pick et al, Circulation 4:468 (1951)), mice (Sullivan et al, J. Clin. Invest. 96:2482–2488 (1995)), rabbits (Kushwaha et al, Metabolism 30:359–366 (1981), Fischer et al, Atherosclerosis 54:177–185 (1985), Haarbo et al, J. Clin. Invest. 87:1274–1279 (1991), Hanke et al, Circulation 94:175–181 (1996), Holm et al, Circulation 98:2731–2737 (1998)), monkeys (Wagner et al, J. Clin. Invest. 88:1995–2002 (1991)), and baboons (Kushwaha et al, Arterioscler. Thromb. 11:23–31 (1991)). Spagnoli and coworkers (Spagnoli et al, Atherosclerosis 82:27–36 (1990)) reported for the first time that high-dose synthetic progestogens alone inhibited atherosclerotic plaque formation in female rabbits fed a cholesterol-enriched diet and concluded that the protective effect was only partly due to alteration in serum cholesterol.

The present invention results, at least in part, from the observation that aortic atherosclerotic plaque load can be decreased in hypercholesterolemic male rabbits with exogenous progesterone as well as with estriol, the decreases in plaque load being independent of alterations in serum lipid levels.

SUMMARY OF THE INVENTION

The present invention relates to a method of treating atherosclerosis. The method comprises administering to a patient in need thereof an effective amount of a progestational agent that has a minimal effect on sex organs or a non-steroidal compound that inhibits macrophages or macrophage function.

Objects and advantages of the present invention will be clear from the description that follows.

DETAILED DESCRIPTION OF THE INVENTION

The present invention relates to a method of treating atherosclerosis (including atherosclerotic cardiovascular disease and stroke) in a mammal (e.g., a human). The method comprises administering to a mammal suffering from atherosclerosis an effective amount of a progestational agent that has a minimal effect on sex organs (e.g., less of an effect that medroxyprogesterone acetate) or a non-steroidal compound that inhibits macrophages or macrophage function (e.g., that inhibits macrophage Fc receptors).

Progestational agents suitable for use in the invention include the progesterone analogs of U.S. Pat. Nos. 4,902,681 and 4,908,358. A preferred such agent is 17-hydroxyprogesterone.

Figure 1:
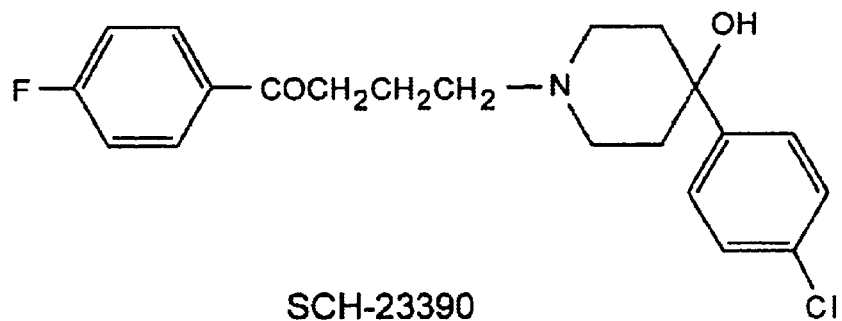
FIG. 1 shows the stucture of haloperidol, SCH-23390 and sulpiride.
Figure 1:
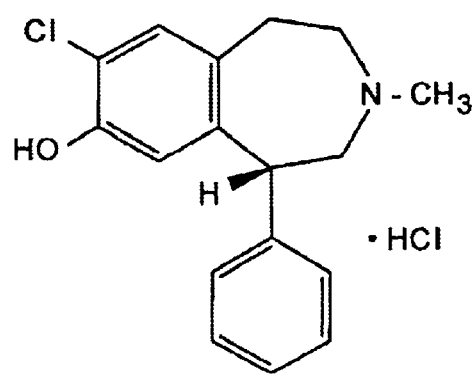
Figure 1:
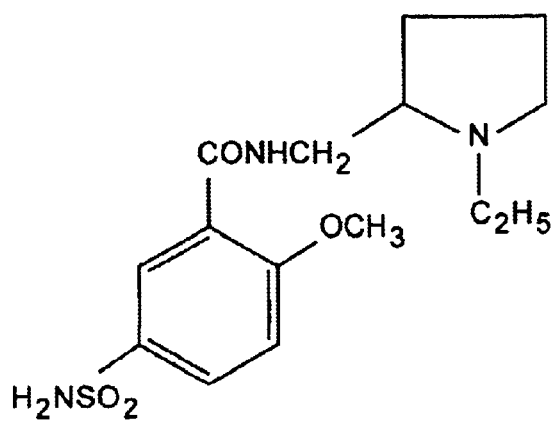

Non-steroidal compounds suitable for use in the present invention include benzazepines and butyrophenones, and pharmaceutically acceptable salts thereof. Benzothiophenes described in U.S. Pat. No. 5,075,321 can also be used. SCH-23390 is an example of a suitable benzazepine and haloperidol is an example of a suitable butyrophenone (see FIG. 1). Analogues of, for example, SCH-23390 or haloperidol, that is, compounds having a similar structure or similar binding affinity for dopamine receptors or comparable capacity to antagonize or stimulate dopamine receptors, can also be used. Structurally similar structures include those wherein an alternative halogen is present as a substituent (e.g., F rather than Cl in the case of SCH-23390) or an alternative $C_1$–$C_4$ alkyl substituent is present (e.g., —$CH_2CH_3$ rather than —$CH_3$ in the case of SCH-23390). Benzazepines and butyrophenones have been shown to bind dopamine receptors (SCH-23390 is a $D_1$ antagonist while haloperidol is a $D_2$ antagonist (Sunahara et al, Br. J. Psych. 163(suppl. 22):31 (1993)). Other $D_1$ and $D_2$ antagonists can be used in accordance with the present method.

Compounds of the invention can be formulated into pharmaceutical compositions suitable for administration via a variety of routes. For example, the compositions can be suitable for oral, rectal, intravenous, or parenteral administration. The compounds can also be formulated so as to be suitable for administration via inhalation. Compositions suitable for such forms of administration are, advantageously, sterile.

Depending on the intended mode of administration, the pharmaceutical composition can be in the form of solid, semi-solid or liquid dosage form, such as, for example, a tablet, pill, capsule, powder, liquid, suspension, or the like, preferably in unit dosage form suitable for single administration of a precise dosage. The pharmaceutical composition can include a conventional pharmaceutical carrier or excipient and a compound according to the invention as an active ingredient. In addition, it can include other medicinal or pharmaceutical agents, carriers, adjuvants, etc.

For oral administration, which is preferred, the pharmaceutical composition can take the form of a solution, suspension, tablet, pill, capsule, powder, sustained release formulation or the like.

For solid pharmaceutical compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like. Liquid pharmaceutically administrable compositions can be prepared by dissolving or dispersing, or otherwise preparing a compound according to this invention and mixing it optionally with a pharmaceutical adjuvant in a carrier, such as, for example, water, saline, aqueous dextrose, glycerol, ethanol, and the like, to thereby form a solution or suspension.

Methods of preparing compositions with a certain amount of active ingredient are known, or will be apparent, to those skilled in this art. For example, see Remington's Pharmaceutical Sciences., Mack Pub. Co., Easter, Pa., 15th Ed. (1975).

Dosage regimens suitable for use in the present invention can be selected so as to achieve the clinical response (e.g., reduction in atherosclerosis plaque load) sought. The doses used will vary depending, for example, on the specific compound employed, the status of the patient and the route of administration. While optimum doses can be readily determined, dosages will generally be selected such that local blood concentrations of 100 to 200,000 pg/ml are achieved, 1,000 to 100,000 pg/ml being preferred, and 10,000 to 100,000 pg/ml being most preferred.

The following non-limiting Examples describes certain aspects of the invention in greater detail.

EXAMPLE 1

Experimental Details

Male New Zealand White rabbits (3.2–4.9 pounds each) were fed a 0.5% cholesterol chow diet for 12 weeks and randomly assigned to five groups (n=6 each); one control group (CG) and four groups treated with estriol (E), haloperidol (H), low-dose 17-hydroxyprogesterone (LDP), or high-dose 17-hydroxyprogesterone (HDP). Serum cholesterol (C) and triglyceride (T) were measured before and after the treatment period in all groups; serum progesterone was determined only in the LDP and HDP groups. After the treatment period, rabbits were euthanized for histomorphometric analysis of aortic plaque load. The rabbits were treated according to the Animal Welfare Act specifications.

Drug Administration

Vehicle only (CG) and vehicle plus steroid (treated groups) were administered daily subcutaneously. Steroid doses were as follows: estriol, 1 mg/kg; haloperidol, 1 mg/kg for 2 weeks, 10 mg/kg for 2 weeks, and 5 mg/kg for 8 weeks; low-dose 17-hydroxyprogesterone, 10 mg/kg; high-dose 17-hydroxyprogesterone, 90 mg/kg. The dose of haloperidol was reduced from 10 mg/kg because of the rabbits' poor tolerance of the higher dose.

Histomorphometric Analysis

Five-micron, serial histologic sections (15 each) of 27 ascending aortas were cut from paraffin blocks, stained with hematoxylin and eosin (H&E) and were studied by light microscopy. Images of tissue sections were captured to a Power Macintosh 7300/200 computer by a Hitachi 3-CCD Color Camera (model HV-C20) attached to a Nikon Eclipse E600 microscope. With digital imaging (IPLap Spectrum, Signal Analytics Corporation, Vienna, Va.), they were then analyzed by manual color segmentation by tracting the endothelial surface (intima), internal elastic lamina, and external elastic lamina of each vessel. From segmented images, intimal and medial areas were computed, allowing calculation of intima to media ratios. Plaque load for each aorta was defined as the ratio of intimal area to medial area (I/M).

Statistical Analysis

Serum lipid levels and I/M were expressed as the mean+ SEM for all animals. The changes in lipid levels before and after the treatment period were compared using paired t-tests. The differences between the treatment groups and controls were compared using analysis of variance (ANOVA) techniques. Repeated Measures ANOVA was used to compare the difference in plaque loads among the five groups. Multiple regression models were used to compare the differences in plaque loads between the four treatment groups and the control group, adjusting for the difference in cholesterol and triglyceride levels. $P<0.05$ was considered statistically significant.

Results

Alteration of Serum Lipids

Over the treatment period, mean serum C increased significantly in all groups. In the HDP group, the increase in serum C (cholesterol) was even greater than that of the CG. Serum T (triglyceride) decreased slightly in the E group but significantly increased in the other groups. Post-treatment serum P levels were significantly higher than baseline levels in the LDP and HDP groups. These data are summarized in Table 1.

Gross and Microscopic Findings

After 91–100 days of treatment, twenty-seven rabbits were euthanized for histomorphometric analysis of aortic plaque load. One rabbit in the E group died after 18 days of treatment, and two rabbits in he H group were sacrificed at 39 and 71 days because of their failure to thrive.

Gross examination of the aortas revealed decreased atherosclerosis in the progesterone and estrogen treated animals. With the control animals, there was about 42% occlusion. With the low dose progesterone there was 6% occlusion and with the high dose progesterone there was 0% occlusion evident.

Fifteen stained serial histologic sections of ascending aorta from each of the twenty-seven surviving rabbits were examined by light microscopy. Atherosclerotic plaques in all specimens revealed variably dense aggregates of macrophage foam cells and α-actin positive smooth muscle cells in a thickened intimal matrix. Rounded foam cells were commonly seen straddling both sides of the focally degenerated internal elastic lamina.

Analysis of Aortic Plaque Loads

Study of the mean I/M for each group, determined by computerized image analysis, revealed significant decreases in all four treatment groups ($P<0.001$ for E, LDP and HDP, and $P=0.02$ for H) when compared to the CG, as shown in Table 2. As further shown in Table 3, both LDP and HDP decreased the atherosclerotic plaque.

Even though the change in serum C and T levels did not have strong relationships with I/M, the values were quite different among the five groups. The group differences were examined, adjusting for the changes in serum C and T levels using a multiple regression model. The aortic plaque load remained lower in all four groups that that of the controls, E ($P=0.052$), H ($P=0.069$), LDP ($P=0.026$), HDP ($P=0.014$), after controlling for the changes in serum C and T levels; the plaque load difference approached statistical significance in the E group and reached the significance level in the HDP group.

TABLE 1

Quantitative Serum Lipid Analysis

| | Treatment groups | | | | |
|---|---|---|---|---|---|
| | CG | E | H | LDP | HDP |
| Cholesterol (pg/dl) | | | | | |
| n: | 5 | 5 | 4 | 6 | 5 |
| B: | 49 | 83.6 | 64.25 | 50.33 | 54 |
| A: | 1421.6 | 1062.8 | 1251.2 | 1441.5 | 2282.67 |
| $\Delta = A-B^1$: | 1372.6 | 979.2 | 1187 | 1391.17 | 2228.67 |
| $\Delta/\Delta_{CG}$: | 1.00 | 0.71 | 0.86 | 1.01 | $1.62^3$ |
| Triglyceride (pg/dl) | | | | | |
| B: | 59.67 | 111 | 86.25 | 71 | 75.8 |
| A: | 543.6 | 96.8 | 476.75 | 560.83 | 1035.33 |
| $\Delta = A-B^2$: | 483.93 | −14.2 | 390.5 | 489.83 | 959.53 |
| $\Delta/\Delta_{CG}$: | 1.00 | −0.03 | 0.81 | 1.01 | 1.98 |
| Progesterone (ng/ml) | | | | | |
| B: | — | — | — | 0.28 | 0.2 |
| A: | — | — | — | 3.03 | 6.48 |
| $\Delta = A-B^1$: | — | — | — | 2.75 | 6.28 |

B--Before treatment;
A--After treatment
1--All changes with $P < 0.05$
2--All changes with $P < 0.05$, except for the E group
3--$P < 0.05$ when compared to the CG

TABLE 2

Morphometric Analysis of Plaque Load

| | Treatment groups | | | | |
|---|---|---|---|---|---|
| | CG | E | H | LDP | HDP |
| n: | 6 | 5 | 4 | 6 | 6 |
| Mean I/M: | 0.81 | 0.02 | 0.29 | 0.42 | 0.47 |
| STD: | 0.43 | 0.04 | 0.39 | 0.21 | 0.25 |
| $(I/M)/(I/M)_{CG}$: | 1.00 | 0.02 | 0.29 | 0.42 | 0.47 |
| P value*: | — | 0.0001 | 0.0198 | 0.0001 | 0.0008 |

*when compared to the control group

TABLE 3

ATHEROSCLEROTIC PLAQUE INHIBITION BY 17-OH PROGESTERONE PLAQUE SIZE IN HYPERCHOLESTEROLEMIC RABBITS

| VEHICLE (RABBIT#) | | | | | |
|---|---|---|---|---|---|
| 1 | 2 | 3 | 4 | 5 | 6 |
| 0.31 | 0.90 | 1.57 | 1.32 | 0.69 | 2.13 |
| | | MEAN = 1.15 | | | |

| LOW DOSE (RABBIT#) (10 mg/kg) | | | | | |
|---|---|---|---|---|---|
| 7 | 8 | 9 | 10 | 11 | 12 |
| 0.66 | 0.30 | 0.84 | 0.85 | 0.14 | 0.52 |
| | | MEAN = 0.55 | | | |

| HIGH DOSE (RABBIT#) (90 mg/kg) | | | | | |
|---|---|---|---|---|---|
| 13 | 14 | 15 | 16 | 17 | 18 |
| 1.37 | 0.11 | 0.33 | 0.23 | 0.18 | 0.02 |
| | | MEAN = 0.37 | | | |

EXAMPLE 2

Inhibition of Human Monocyte/Macrophage Fcγ Receptor Mediated Phagocytosis

The agents to be tested (haloperidol, SCH-23390 and sulpiride) were incubated with human monocytes isolated using lymphocyte separation medium. Incubation was for 90 min at 37° C. Buffer (PBS) treated cells served as a control. At the end of the incubation period, monocytes were exposed to IgG-sensitized cells in accordance with the phagocytic assay of Indik et al, Blood 86:4389 (1995). The results are as shown in Table 4.

TABLE 4

| | % Phagocytic Cells[1] | PI[2] |
|---|---|---|
| Buffer (PBS) treated control | 42% | 105 |
| Haloperidol (50 μM PBS/methanol) | 0% | 0 |
| SCH-23390 (50 μM PBS/methanol) | 16% | 38 |
| Sulpiride (500 μg/ml PBS/methanol) | 59% | 232 |

[1] % Phagocytic cells = Percent of monocytes/macrophages phagocytosing IgG sensitized cells
[2] PI = Phagocytic index = The number of ingested IgG-sensitized cells per 100 monocytes.

No change in expression of the monocyte Fcγ receptor FcγRI, FcγRII or Fc↓RIIIA was noted using flow cytometry analysis.

All documents cited above are hereby incorporated in their entirety by reference.

One skilled in the art will appreciate from a reading of this disclosure that various changes in form and detail can be made without departing from the true scope of the invention.

What is claimed is:

1. A method of reducing an atherosclerotic plaque load in the vessels of a patient comprising administering to a patient in need of such reduction 16-methylprogesterone in an amount so that said reduction is effected.

2. A method of reducing an atherosclerotic plaque load in the vessels of a patient comprising administering to a patient in need of such reduction 5α-pregnan-3,20-dione in an amount so that said reduction is effected.

* * * * *